United States Patent [19]

Parker

[11] 4,011,334
[45] Mar. 8, 1977

[54] USE OF SUBSTITUTED FURAN AND THIOPHENE CARBOXALDEHYDES AS HYPOLIPIDEMIC AGENTS

[75] Inventor: Roger Alan Parker, Cincinnati, Ohio

[73] Assignee: Richardson-Merrell Inc., Wilton, Conn.

[22] Filed: Oct. 3, 1975

[21] Appl. No.: 619,305

[52] U.S. Cl. .......................... 424/275; 260/329 S; 260/332.2 C; 260/332.3 C; 260/347.2; 260/347.3; 424/285
[51] Int. Cl.² .................. A61K 31/34; A61K 31/38
[58] Field of Search ........................... 424/275, 285

[56] References Cited
UNITED STATES PATENTS

| | | | |
|---|---|---|---|
| 3,399,199 | 8/1968 | Grier | 260/268 PH |
| 3,695,899 | 10/1972 | Lee et al. | 424/275 X |
| 3,953,601 | 4/1976 | Bondesson et al. | 424/275 |

OTHER PUBLICATIONS

Chemical Abstracts I, vol. 53:21871–21872, (1959).
Chemical Abstracts II, vol. 54:5694, (1960).
Chemical Abstracts III, vol. 55:6465, (1961).

Primary Examiner—Albert T. Meyers
Assistant Examiner—Vera C. Clarke
Attorney, Agent, or Firm—L. Ruth Hattan; Eugene O. Retter; George W. Rauchfuss, Jr.

[57] ABSTRACT

Substituted thiophene and furan carboxaldehydes of the following general Structure are useful as hypolipidemic agents:

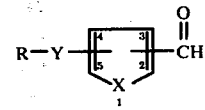

wherein Y is selected from oxygen and divalent sulfur; R is selected from a straight or branched saturated hydrocarbon chain having from 10 to 20 carbon atoms and a straight or branched unsaturated hydrocarbon chain having from 10 to 20 carbon atoms and from 1 to 4 double bonds; X is selected from oxygen and divalent sulfur.

7 Claims, No Drawings

USE OF SUBSTITUTED FURAN AND THIOPHENE CARBOXALDEHYDES AS HYPOLIPIDEMIC AGENTS

FIELD OF INVENTION

This invention relates to the use of substituted thiophene and furan carboxaldehydes as hypolipidemic agents.

DESCRIPTION OF PRIOR ART

The compounds described herein are generally known in the art. The following references report compounds described herein: West German Pat. No. 2,210,230 describes compounds wherein the substituent R is a straight or branched saturated or unsaturated hydrocarbon group, and Y is sulfur as being useful as antimicrobial and cytostatic agents. In Monatsber. Deut. Acad. 1, 180–8 (1959) compounds wherein R is a saturated hydrocarbon group, and Y is sulfur are reported as starting materials. U.S. Pat. No. 3,399,199 describes compounds wherein R is a saturated hydrocarbon group, and Y is oxygen as starting materials. To applicant's knowledge the use of compounds described herein as hypolipidemic agents has not been described previously.

SUMMARY OF INVENTION

Compounds of the following general Formula I are useful as hypolipidemic agents:

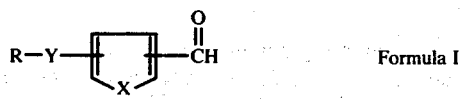

Formula I wherein Y is selected from oxygen and divalent sulfur; R is selected from a straight or branched saturated hydrocarbon chain having from 10 to 20 carbon atoms and a straight or branched unsaturated hydrocarbon chain having from 10 to 20 carbon atoms and from 1 to 4 double bonds; X is selected from oxygen and divalent sulfur.

DETAILED DESCRIPTION OF INVENTION

In the above general Formula I the substituent group represented by R-Y- and the carboxaldehyde function may be attached at any of the positions 2-, 3-, 4-, or 5- of the thiophene or furan ring with the proviso that the carboxaldehyde function and the group R-Y- are not attached to the same carbon atom.

R may be a straight or branched saturated hydrocarbon chain of from 10 to 20 carbon atoms in which case the substituent group R-Y- may be represented as $C_nH_{2n+1}Y$ wherein Y is oxygen or divalent sulfur, and n is an integer of from 10 to 20, and the hydrocarbon chain may be straight or branched. The straight or branched saturated hydrocarbon chain described herein may also be described as a straight or branched alkyl group having from 10 to 20 carbon atoms.

R may also be a straight or branched unsaturated hydrocarbon chain having from 10 to 20 carbon atoms and from 1 to 4 double bonds in which case the substituent group R-Y- may be represented as $C_nH_{2n-m}Y-$ wherein Y is oxygen or divalent sulfur, n is an integer of from 10 to 20, m is the integer 1, 3, 5 or 7 to give either 1, 2, 3, or 4 double bonds in the hydrocarbon chain which may be straight or branched. The staight or branched hydrocarbon chain described herein could also be described when 1 double bond is present, as a straight or branched alkenyl group having from 10 to 20 carbon atoms; when 2 double bonds are present, as a straight or branched alkadienyl group having from 10 to 20 carbon atoms; when 3 double bonds are present, as a straight or branched alkatrienyl group having from 10 to 20 carbon atoms; and when 4 double bonds are present as a straight or branched alkatetraenyl group having from 10 to 20 carbon atoms.

Illustrative examples of straight or branched saturated hydrocarbon chains having from 10 to 20 carbon atoms which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl, 3-methyloctadecyl, nonadecyl and didecyl. Illustrative examples of straight or branched unsaturated hydrocarbon chains having from 10 to 20 carbon atoms and from 1 to 4 double bonds which R may represent are, for example 10-undecenyl, 9,12-octadecadienyl, 3,7,11-trimethyl-2,6,10-octatrienyl, 3,7-dimethyl-2,6-octadienyl, 5,9-dimethyl-2,4,8-decatrienyl, 3,7-dimethyl-6-octenyl, 1,2,5,9-tetramethyl-2,4,8-decatrienyl and 11-didecenyl. The use of both the cis- and trans-isomers of the unsaturated hydrocarbon chains are included within the scope of this invention.

It is apparent from the above general Formula I that the compounds described herein are alkoxy- and alkylthiothiophene carboxaldehydes as represented by the following general Formula II or are alkoxy- and alkyethio- furan carboxaldehydes as represented by the following general Formula III.

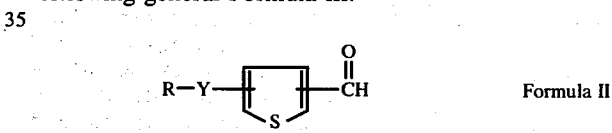

Formula II

In the above general Formula II R and Y have the meanings defined in general Formula I.

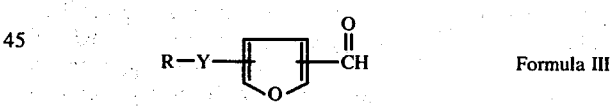

Formula III

In the above general Formula III R and Y have the meanings defined in general Formula I.

The use of the compounds represented by each of Formulas II and III as hypolipidemic agents represents a preferred embodiment of this invention. A more preferred embodiment of this invention is the use as hypolipidemic agents of the compounds of general Formulas II and III wherein the R-Y- substituent is attached to the 5-position of the thiophene or furan ring, and the carboxaldehyde function is attached to the 2-position of the thiophene or furan ring as illustrated by the following general Formula IV.

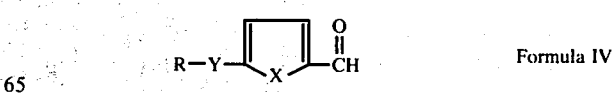

Formula IV

In the above general Formula IV the substituent groups R, Y and X have the meanings defined in general Formula I. The use of the compounds for general Formula IV wherein the R substituent has from 12 to 16 carbon atoms represents a more preferred embodiment of this invention.

Illustrative examples of compounds of this invention are, for example, 5-decyloxy-2-furancarboxaldehyde, 5-tetradecyloxy-2-thiophenecarboxaldehyde, 5-(trans-9-octadecenyloxy)-2-thiophenecarboxaldehyde, 5-dodecyloxy-2-thiophenecarboxaldehyde, 3-tetradecyloxy-2-thiophenecarboxaldehyde, 5-(10-undecenylthio)-2-thiophenecarboxaldehyde, 5-octadecylthio-2-thiophenecarboxaldehyde, 5-tetradecylthio-2-thiophenecarboxaldehyde, 4-dodecylthio-2-thiophenecarboxaldehyde, 3-tridecyloxy-2-thiophenecarboxaldehyde, 5-hexadecyloxy-2-thiophenecarboxaldehyde, 2-heptadecyloxy-3-furancarboxaldehyde, 4-undecylthio-3-thiophenecarboxaldehyde, 5-hexadecyloxy-2-furancarboxaldehyde, 5-pentadecylthio-2-thiophenecarboxaldehyde, 5-tetradecyloxy-2-furancarboxaldehyde, 5-dodecyloxy-2-furancarboxaldehyde, 4-dodecyloxy-2-thiophenecarboxaldehyde, 5-undecyloxy-2-thiophenecarboxaldehyde, 5-nonadecyloxy-2-thiophenecarboxaldehyde, 5-didecyloxy-2-thiophenecarboxaldehyde, 3-didecyloxy-2-furancarboxaldehyde, 5-(10-undecenyloxy)-2-thiophenecarboxaldehyde, 4-(trans,trans-1,2,5,9-tetramethyl-2,4,8-decatrienyloxy)-2-thiophenecarboxaldehyde, 5-(cis,cis-9,12-octacecadienyloxy)-3-furancarboxaldehyde and 5-(3,7-dimethyl-6-octenyloxy)-2-thiophenecarboxaldehyde.

The compounds described herein are useful as hypolipidemic agents in that they reduce blood lipids, particularly cholesterol and triglycerides without concurrent accumulation of desmosterol. These compounds can be administered to animals, mammals, rats, cats, dogs, cattle, horses, and humans and can be useful in the treatment of hyperlipidemic states such as are encountered in patients with cardiovascular diseases that can result in heart failure and stroke. As used herein, the term patient is intended to mean the animal or mammal being treated.

The utility of the compounds disclosed herein is demonstrated in young male rats of the Wistar strain initially weighing about 175 grams which are given free excess to a diet containing 0.15 percent by weight of test compound, that is, a compound of general Formula I. This diet is prepared by mixing the test compound with commercial Purina Chow. (Trade Mark of Ralston-Purina Company., St. Louis, Mo). Groups of animals are given these diets for either 4 to 10 days. Control groups of 6 rats each are given Purina Chow to which no test compound has been added. At the end of the treatment, all rats are bled by cardiac puncture, and the plasma is analyzed for cholesterol and triglyceride content.

The compounds of this invention can be administered orally or parenterally either alone or in the form of pharmaceutical preparations. Pharmaceutical preparations containing conventional pharmaceutical carriers and as active ingredients compounds of this invention can be employed in unit dosage form such as solids, for example, tablets, capsules and pills or liquid solutions, suspensions, or emulsions for oral and parenteral administration. The dosage unit administered can be any lipid lowering effective amount. The quantity of the compound administered can vary over a wide range to provide from about 0.5 mg/kg (milligram per kilogram) to about 300 mg/kg of body weight of the patient per day, and preferably, from about 10 mg/kg to 30 mg/kg of body weight of the patient per day, to achieve the desired effect. Unit doses can contain from about 50 mg to 1 g (gram) of a compound described herein and may be administered, for example, from 1 to 4 times daily. Illustrative examples of pharmaceutical preparations of the compounds described herein are the following.

An illustrative composition for tablets is as follows:

| | Per Tablet |
|---|---|
| (a) 5-(tetradecyloxy)-2-thiophenecarboxaldehyde | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

An illustrative composition for a parenteral injection is the following wherein the quantities are on a weight to volume basis.

| | Amount |
|---|---|
| (a) 5-(tetradecyloxy)-2-furancarboxaldehyde | 100.0 mg |
| (b) peanut oil | 1 ml |

The active ingredient is suspended in the oil and to the suspension is added an appropriate amount of a preservative such as methylparaben or propylparaben.

An illustrative composition for hard gelatin capsules is as follows:

| | Amount |
|---|---|
| (a) 5-(tetradecylthio)-2-thiophenecarboxaldehyde | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

An illustrative composition for pills is the following:

| | Per Pill |
|---|---|
| (a) 5-(tetradecylthio)-2-furancarboxaldehyde | 200 mg |
| (b) corn starch | 130 mg |
| (c) liquid glucose | 20 ml |

The pills are formed by blending the active ingredient (a) and the corn starch then adding the liquid glucose with thorough kneading to form a plastic mass from which the pills are cut and formed.

The compounds described herein may be prepared by chemical or catalytic reduction of the corresponding R-Y-substituted carboxylic acid halide or tertiary amide by methods generally described in J. March, *Advanced Organic Chemistry:Reactions, Mechanism and Structure*, McGraw-Hill, pp. 351 and 352 (1968).

Reduction of the corresponding carboxylic acid halides, for example, the acid chloride using a catalytic hydrogenation method to give the aldehyde compound is known as the Rosemund reduction and is the most common way to prepare the aldehydes. A suitable catalyst for this reaction is palladium-BaSO$_4$ in a ratio of 1 part catalyst to 5 to 10 parts of acid chloride. This reaction may be carried out with or without a regulator such as quinoline-sulfur. Suitable solvents for this reaction are dry solvents selected from aromatic hydrocarbons, such as, benzene, toluene and xylene, nonaromatic hydrocarbons such as, decalin and ethers, such as, diethylether. This reaction may be carried out at temperatures of from room temperature, that is, about 25° C to the reflux temperature of the solvent and the reaction time may vary from about 15 minutes to 24 hours. Reduction of the tertiary carboxamide or acid halide using a metal hydride reducing agent is another useful method for obtaining the aldehyde compounds. The reaction can be carried out in ether solvents, such as, diethylether, tetrahydrofuran, dioxane and glyme or aromatic hydrocarbon solvents such as, benzene and toluene. The reaction temperature may vary from 0° C to the reflux temperature of the solvent, and the reaction time may vary from about 15 minutes to 24 hours. The carboxylic acid halides and carboxamide derivatives can be prepared from the corresponding acid by procedures generally known in the art. The carboxamide derivatives can be isolated or formed in situ. The corresponding carboxylic acid derivatives can be prepared by aromatic nucleophilic substitution as generally described in the above-cited March reference at page 500 as outlined below.

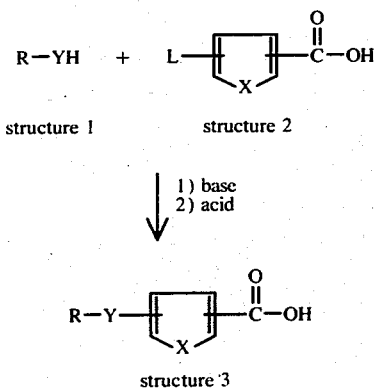

In the above general reaction R, Y and X have the meanings defined in general Formula 1 and L represents a leaving group such as nitro, fluoro, chloro, bromo, iodo, the preferred leaving group being chloro. The substituent group L on compounds of structure 2 and R-Y- on compounds of structure 3 and the

group may be attached at the 2-, 3-, 4- or 5-position of the thiophene or furan ring, with the proviso that both L or R-Y- and

are not attached to the same position of the thiophene or furan ring.

The above reaction may be carried out with or without a solvent. Suitable solvents for the reaction include benzene, xylene, toluene, chlorinated aromatic hydrocarbons, such as, chlorobenzene, ethers, such as, bis(2-methoxyethyl) ether, 1,2-dimethoxyethane or anisole, dimethylformamide, dimethylacetamide, 1-methyl-2-pyrrolidone or pyridine. Preferred solvents are xylene and dimethylacetamide. Copper metal or a salt such as cuprous chloride may be optionally added to the reaction. Suitable basis for the reaction include sodium or potassium metal, sodium hydride, potassium amide, potassium tert-butylate or other strong bases, such as, potassium carbonate, potassium hydroxide, sodium hydroxide, and sodium carbonate. The temperature of the reaction varies from about room temperature that is about 25° C, to reflux temperature of the solvent, and the reaction time varies from about 1 hour to about 7 days, and following completion of the reaction the carboxylate salt derivative is treated with a mineral or organic acid to give compounds of structure 3

Alcohols as represented by compounds of structure 1 which find use in the above general reaction are commercially available or may be prepared by reduction of the corresponding carboxylic acid or aldehyde.

The thiophenecarboxylic acid derivatives as represented by compounds of structure 2 wherein X is sulfur may be prepared by several methods as described in the *Chemistry of Heterocyclic Compounds, Thiophene and Its Derivatives*, by H. D. Hartough, Interscience Publishers, Inc., N.Y., pp. 379–381 (1952). The furoic acid derivatives as represented by compounds of structure 2 wherein X is oxygen may be prepared by several methods as described in *The Furans*, by A. P. Dunlop and F. N. Peters, Rheinhold Publishing Corp., pp. 80 to 169 (1953).

The thiophenecarboxaldehydes described herein wherein the R-Y- substituent is attached to the 5-position of the thiophene ring and the carboxaldehyde function is attached to the 2-position of the thiophene ring may also be prepared by treating an appropriate R-Y- substituted thiophene derivative with N-methylformanilide and phosphorus oxychloride followed by water hydrolysis as generally described, for example, in Fieser and Fieser, Advanced Organic Chemistry, Reinhold Publishing Corporation, New York (1961). The R-Y- substituted thiophene derivatives wherein Y represents sulfur can be obtained in the manner described by E. Profft, Chemiker-Zeitung, 82, 298 (1958) and wherein Y represents oxygen can be prepared from the 3-thiolene-2-one (R. T. Hawkins, Journal Heterocyclic Chemistry, 11, (3) 291–4 (1974)) with a suitable alkyl halide, alkyl mesylate or alkyl tosylate in the presence of a base, for example, sodium hydride, potassium amide, potassium tert-butylate, sodium or potassium metal, potassium carbonate, sodium carbonate, triethylamine, or pyridine to yield the 2-alkoxythiophene intermediates. This reaction may be carried out with or without a solvent. Suitable solvents include pyridine, benzene, xylene, chlorobenzene, ethers, for example, bis(2-methoxyethyl)ether or anisole, dimethylformamide, dimethylacetamide, and hexamethylphosphoric triamide. The alkyl halide may be, for example, alkyl chloride, alkyl bromide, or alkyl iodide. The alkyl moiety in the alkyl halide, the alkyl mesylate, or the alkyl tosylate is a hydrocarbon radical containing from 10 to 20 carbon atoms which may be straight or branched and which may be saturated in which case it may contain from 1 to 4 double bonds.

The following specific examples are illustrative of the compounds described herein.

EXAMPLE 1

5-Hexadecyloxy-2-thiophenecarboxaldehyde

A. A mixture of 20 g (0.2 mole) of 3-thiolen-2-one[R. T. Hawkins, J. Heterocyclic Chemistry 11, 291-4 (1974)], 61.1 g (0.2 mole) of 1-bromohexadecane, and 9.6 g (0.2 mole) of sodium hydride (50% in oil) in dry benzene is refluxed with stirring for 24 hours after which the solvent is removed and the product is distilled to give 2-hexadecyloxythiophene.

B. To a cooled mixture of 27 g of N-methylformanilide in 27 g (0.176 mole) of phosphorusoxy chloride is added 32.5 g (0.1 mole) of 2-hexadecyloxythiophene. The mixture is warmed to 70° C under vacuum (10 mm Hg). The mixture is allowed to stand at 60° to 70° 20 C for 7 hours, then overnight at room temperature after which the mixture is stirred into 100 g of ice. The mixture is extracted into benzene, washed with water, dried over sodium sulfate and distilled in vacuo to give 5-hexadecyloxy-2-thiophenecarboxaldehyde.

EXAMPLE 2

5-(3,7,11,15-Tetramethylhexadecyloxy)-2-furancarboxaldehyde

A. A mixture of 59.8 g (0.2 mole) of 3,7,11,15-tetramethyl-1-hexadecanol and 19.2 g (0.4 mole) of sodium hydride (50% in oil) in 1 liter of toluene is refluxed with stirring for 2 hours then cooled to room temperature. To the mixture 29.3 g (0.2 mole) of 5-chloro-2-furoic acid is added and the mixture is refluxed with stirring for 24 hours. Upon cooling to room temperature the mixture is acidified with glacialacetic acid and water is added. The toluene layer is evaporated and allowed to crystallize to give 5-(3,7,11,15-tetramethylhexadecyloxy)-2-furoic acid.

B. A mixture of 57.2 g (0.14 mole) of 5-(3,7,11,15-tetramethylhexadecyloxy)-2furoic acid in 300 ml of thionyl chloride is heated to reflux for 1 hour, and the excess thionyl chloride is removed by distillation to give 5-(3,7,11,15-tetramethylhexadecyloxy)-2-furancarboxylic acid chloride with is combined with 2.8 g of 2% palladium-BaSO$_4$ catalyst, 0.6 g of quinoline-sulfur in 800 ml of xylene. A slow stream of hydrogen gas is passed through the mixture until hydrogen chloride is no longer evolved (about 8 hours). After cooling, the catalyst is removed by centrifuging, and the solvent is removed under reduced pressure. The residue is distilled to give 5-(3,7,11,15-tetramethylhexadecyloxy)-2-furancarboxaldehyde.

EXAMPLE 3

5-(Dodecylthio)-2-thiophenecarboxaldehyde

A. A mixture of 40.5 g (0.2 mole) of 1-dodecanethiol (laurylmercaptan) in 19.2 g (0.4 mole) of sodium hydride (50% in oil) in 1 liter of toluene is refluxed with stirring for 1 hour then cooled to room temperature. To the mixture 32.5 g (0.2 mole) of 5-chloro-2-thiophenecarboxylic acid is added and the mixture is refluxed with stirring for 24 hours after which the mixture is cooled to room temperature and acidified with 5% aqueous hydrochloric acid. Water is added, and the toluene layer is separated, dried over sodium sulfate and evaporated to give 5-(dodecylthio)-2-thiophenecarboxylic acid.

B. A mixture of 32.8 g (0.1 mole) of 5-(dodecylthio)-2-thiophenecarboxylic acid in 500 ml of tetrahydrofuran is stirred in an ice bath. To the cooled mixture is slowly added 19.5 g (0.12 mole) of 1,1'-carbonyldiimidazole. The reaction mixture is refluxed for 2 hours, then cooled in an ice bath. Ether and ice water are added to the mixture and the layers separated. The ether layer is washed with ice water and 5% aqueous sodium bicarbonate then dried over solium sulfate and evaporated to dryness to give 1-[5-(dodecylthio)-2-thienylcarbonyl]-1H-imidazole. To a stirred mixture of 37.9 g (0.1 mole) of the crude 1-[5-dodecylthio)-2-thienylcarbonyl]-1-H-imidazole in 500 ml of tetrahydrofuran cooled to −20° C is slowly added 0.95 g (0.25 mole) of lithium aluminum hydride in 100 ml of ether. After 1 hour 100 ml of 5% aqueous hydrochloric acid is added dropwise with stirring after which the mixture is warmed to room temperature, diluted with water and ether and extracted. The ether layer is washed with 5% aqueous hydrochloric acid water and 5% aqueous sodium bicarbonate then dried over sodium sulfate and evaporated to dryness to give 5-(dodecylthio)-2-thiophenecarboxaldehyde.

When in the procedure of Example 2 (B) an appropriate amount of an acid listed in the following Table 1 is substituted for 5-(3,7,11,15-tetramethylhexadecyloxy)-2-furoic acid the respective products listed in Table 1 are obtained.

TABLE 1

| ACID | PRODUCT |
|---|---|
| 5-(trans-trans-3,7,11-trimethyl-2,6,10-dodecatrienyloxy)-2-thiophenecarboxylic acid | 5-(trans-trans-3,7,11-trimethyl-2,6,10-dodecatrienyloxy)-2-thiophenecarboxaldehyde |
| 5-(cis-cis-9,12-octadecadienylthio)-2-thiophenecarboxylic acid | 5-(cis-cis-9,12-octadecadienylthio)-2-thiophenecarboxaldehyde |
| 4-hexadecylthio-2-thiophenecarboxylic acid | 4-hexadecylthio-2-thiophenecarboxaldehyde |
| 2-didecyloxy-3-thiophenecarboxylic acid | 2-didecyloxy-3-thiophenecarboxaldehyde |
| 5-tetradecyloxy-2-thiophenecarboxylic acid, M.P. 95–96° C | 5-tetradecyloxy-2-thiophenecarboxaldehyde |
| 5-tetradecylthio-2-thiophenecarboxylic acid, M.P. 106–108° C | 5-tetradecylthio-2-thiophenecarboxaldehyde |
| 5-(trans-3,7-dimethyl-2,6-octadienyloxy)-3-furoic acid | 5-(trans-3,7-dimethyl-2,6-octadienyloxy)-3-furancarboxaldehyde |
| 5-(10-undecenylthio)-2-furoic acid | 5-(10-undecenylthio)-2-furancarboxaldehyde |
| 5-heptadecyloxy-3-furoic acid | 5-heptadecyloxy-3-furancarboxaldehyde |
| 5-tetradecylthio-2-furoic acid, M.P. 84–86° C | 5-tetradecylthio-2-furancarboxaldehyde |
| 5-octadecyloxy-2-furoic acid, M.P. 117–118° C | 5-octadecyloxy-2-furancarboxaldehyde |
| 5-dodecyloxy-2-furoic acid, M.P. 122–123° C | 5-dodecyloxy-2-furancarboxaldehyde |
| 5-decyloxy-2-furoic acid, | 5-decyloxy-2-furancarboxalde- |

TABLE 1-continued

| ACID | PRODUCT |
| --- | --- |
| M.P. 124–126° C | hyde |
| 5-(cis-9-octadecenyloxy)-2-furoic acid, M.P. 93–96° C | 5-(cis-9-octadecenyloxy)-2-furancarboxaldehyde |
| 5-hexadecyloxy-2-furoic acid, M.P. 118–119° C | 5-hexadecyloxy-2-furancarboxaldehyde |
| 5-tetradecyloxy-2-furoic acid, M.P. 112–115° C | 5-tetradecyloxy-2-furancarboxaldehyde |

Similarly, when an appropriate amount of an acid listed in the above Table 1 is substituted for 5-dodecylthio-2-thiophenecarboxylic acid in the procedure of Example 3 (B) the respective products listed in Table 1 are obtained.

I claim:

1. A method of reducing the lipid concentration in the blood of a patient in need thereof which comprises orally or parenterally administering to said patient a lipid-lowering effective amount of a compound of the formula:

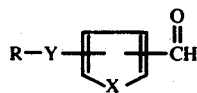

wherein Y is selected from the group consisting of oxygen and divalent sulfur, R is selected from the group consisting of a straight or branched saturated hydrocarbon chain having from 10 to 20 carbon atoms and a straight or branched unsaturated hydrocarbon chain having from 10 to 20 carbon atoms and from 1 to 4 double bonds, and X is selected from the group consisting of oxygen and divalent sulfur.

2. The method of claim 1 wherein X is oxygen.

3. The method of claim 1 wherein X is divalent sulfur.

4. A method of reducing the lipid concentration in the blood of a patient in need thereof which comprises orally or parenterally administering to said patient a lipid-lowering effective amount of a compound of the formula:

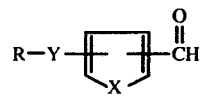

wherein Y is selected from the group consisting of oxygen and divalent sulfur, R is selected from the group consisting of a straight or branched saturated hydrocarbon chain having from 10 to 20 carbon atoms and a straight or branched unsaturated hydrocarbon chain having from 10 20 carbon atoms and from 1 to 4 double bonds, and X is selected from the group consisting of oxygen and divalent sulfur.

5. The method of claim 4 wherein R has from 12 to 16 carbon atoms.

6. The method of claim 5 wherein X is oxygen.

7. The method of claim 5 wherein X is divalent sulfur.